United States Patent
Ishihara et al.

(10) Patent No.: US 6,706,843 B1
(45) Date of Patent: Mar. 16, 2004

(54) METHOD FOR SEPARATING AND RECOVERING DIMETHYL TEREPHTHALATE AND ETHYLENE GLYCOL FROM POLYESTER WASTE

(75) Inventors: Kenichi Ishihara, Matsuyama (JP); Kenji Ishida, Matsuyama (JP); Masanori Miyamoto, Matsuyama (JP); Minoru Nakashima, Matsuyama (JP); Kazuhiro Sato, Matsuyama (JP); Hideo Hasegawa, Matsuyama (JP)

(73) Assignee: Teijin Limited, Osaka (JP)

( * ) Notice: Subject to any disclaimer, the term of this patent is extended or adjusted under 35 U.S.C. 154(b) by 103 days.

(21) Appl. No.: 10/111,010

(22) PCT Filed: Oct. 19, 2000

(86) PCT No.: PCT/JP00/07289

§ 371 (c)(1),
(2), (4) Date: Apr. 19, 2002

(87) PCT Pub. No.: WO01/30729

PCT Pub. Date: May 3, 2001

(30) Foreign Application Priority Data

| Oct. 22, 1999 | (JP) | 11/300619 |
| Dec. 22, 1999 | (JP) | 11/364479 |
| Dec. 22, 1999 | (JP) | 11/364480 |

(51) Int. Cl.[7] ............ C08J 11/04; C08F 6/00; C08C 67/48

(52) U.S. Cl. ............ 528/48.5; 528/275; 528/308.6; 528/488; 528/490; 528/495; 528/501; 528/502; 528/503; 560/78; 526/65; 526/67; 526/71

(58) Field of Search ............ 521/46.5; 528/275, 528/308.6, 486, 490, 495, 501, 502, 503; 560/78; 526/65, 67, 71

(56) References Cited

U.S. PATENT DOCUMENTS

| 5,430,174 A | | 7/1995 | Shono et al. |
| 5,481,024 A | * | 1/1996 | Hertenstein et al. .......... 560/78 |
| 5,504,122 A | | 4/1996 | Michel et al. |
| 5,712,410 A | | 1/1998 | Naujokas |
| 6,136,869 A | * | 10/2000 | Ekart et al. ................ 521/48.5 |
| 6,472,557 B1 | * | 10/2002 | Pell et al. .................... 562/483 |

FOREIGN PATENT DOCUMENTS

| EP | 667 335 | 8/1995 |
| JP | 43-2088 | 1/1968 |
| JP | 07-309809 | 11/1995 |
| JP | 8-259728 | 10/1996 |
| JP | 11-21374 | 1/1999 |
| JP | 11-302208 | 11/1999 |
| JP | 2000-169623 | 6/2000 |

* cited by examiner

Primary Examiner—Samuel A. Acquah
(74) Attorney, Agent, or Firm—Rader, Fishman & Grauer PLLC

(57) ABSTRACT

For separation and recovery of dimethyl terephthalate (DMT) and ethyiene glycol (EG) from polyester waste containing foreign materials, the polyester waste is treated in EG containing a polyester depolymerization catalyst, a solid foreign material fraction floated on the surface of the resultant reaction solution is removed and the residual solid foreign material fraction is removed from the remaining solution fraction. The remaining solution fraction is distilled and concentrated and the distilled EG is recovered. A transesterification reaction catalyst and methanol are mixed into the distillation residue. The resultant reaction mixture is recrystallized and subjected to centrifugal separation to separate the reaction mixture into the DMT cake and a mixture solution, and then the cake is distilled whereby high-purity DMT is recovered. The residual mixture solution is subjected to distillation treatment for recovery of the methanol, and the distillation residue is distilled to recover EG.

15 Claims, 2 Drawing Sheets

METHOD FOR SEPARATING AND RECOVERING DIMETHYL TEREPHTHALATE AND ETHYLENE GLYCOL FROM POLYESTER WASTE

TECHNICAL FIELD

The present invention relates to a process for separation of effective components from polyester waste (which may be either valuable or valueless substances). More specifically, the present invention relates to a process for separation and recovery of effective components such as dimethyl terephthalate and ethylene glycol from polyester waste which contains polyethylene terephthalate as the major component along with a foreign material, with a high efficiency.

BACKGROUND ART

Because of their excellent chemical stability, polyalkylene terephthalates are produced and used in large quantities for common materials such as fibers, films, resins and the like, as well as in the field of food packaging, and as bottles for drinking water, carbonated beverages and the like.

However, the costs of processing fiber, film and resin product waste or off-specification materials such as polyalkylene terephthalates (hereinafter also referred to simply as "polyester waste"), which are produced in large quantities with increasing production output and usage, are associated with higher product cost, while their processing is also a major problem for modern society, and therefore various recycling methods have been proposed for material recycling, thermal recycling, chemical recycling and the like.

Although material recycling whereby polyester waste is converted to low grade quality substances by melt molding has largely improved the situation for "disposables", the obtained recycled products undergo further quality reduction when recycled again, and therefore their uses are limited and it has been difficult to avoid final disposal of polyalkylene terephthalates.

Another method employed is thermal recycling, whereby polyester waste is used as a fuel. This method offers the advantage of reutilizing the heat of combustion of the polyester waste, but since burn-off of the polyester waste cannot be avoided, it entails the problems of loss of the polyalkylene terephthalate starting material and generation of carbon dioxide, and is therefore not preferred from the standpoint of conservation of resources and preservation of the environment.

Chemical recycling is also being investigated as an alternative to the two types of recycling methods described above, whereby polyester waste is converted to its constituent components which are then recovered and again subjected to polymerization reaction to produce polyester for reuse.

Specifically, there is known a process in which the recovered polyester waste is reacted with methanol (hereinafter also abbreviated as "MeOH") and is recovered as dimethyl terephthalate (hereinafter also abbreviated as "DMT") and alkylene glycols, and a process in which the recovered polyester waste is hydrolyzed in the presence of an alkali compound and the resulting terephthalic acid and alkylene glycols are recovered. Such chemical recycling processes allow recycled reuse of compounds with essentially no loss, and thus offer advantages for reutilization of resources.

However, polyester waste delivered from the distribution industry and households usually contains foreign materials including chlorine-containing polymers such as polyvinyl chloride and polyvinylidene chloride (these will hereinafter be collectively referred to as "PVC"), colored polyester materials and polyolefins.

It has been difficult to avoid inclusion of such foreign materials even in the polyethylene/alkylene terephthalate portion (hereinafter also referred to as "polyalkylene terephthalate scrap") which is sorted from polyester waste. These included foreign materials may cause various problems such as generation of decomposition gases (for example, hydrogen chloride gas) during the heating and reaction operations for the polyalkylene terephthalate scrap, or may melt and solidify in the recovery apparatus leading to damage to the instruments or clogging and adhesion inside the instruments. In addition, formation of organic chlorine compounds from hydrogen chloride gas can notably lower the quality of the recovered DMT and alkylene glycols.

For chemical recycling, therefore, effective reuse of polyalkylene terephthalates contained in polyester waste has required separation of the foreign materials in the polyester waste.

A conventional process for recovery of polyester waste, which is widely known as the glycolysis/transesterification reaction process and which is employed industrially, is a process of depolymerizing the polyalkylene terephthalates with ethylene glycol (hereinafter abbreviated as "EG") and then subjecting them to a transesterification reaction with MeOH to obtain DMT.

During removal of the foreign materials, however, thermal decomposition of PVC, for example, becomes notable from about 195° C., and it has therefore been difficult to apply chemical recycling of PVC-containing polyalkylene terephthalate scrap as a result of the PVC decomposition that occurs by the above-mentioned glycolysis process that is usually carried out at 195 to 240° C. Moreover, when chemical recycling is applied to polyester waste containing colored polyalkylene terephthalates, partial decomposition of the colored substances reduces the quality of the recovered compounds.

In addition, in the case of polyolefin-containing polyester waste, melting or solidification of the polyolefins occurs under the processing conditions for the conventional glycolysis/transesterification reaction, causing such problems as clogging of the apparatus and hampered operation and, therefore, difficulties have plagued the industrial treatment of polyolefin-including polyester waste by conventional polyester recovery processes.

As a means of solving this problem, U.S. Pat. No. 5,504,122 proposes a process of adding an alkali compound to hydrogen chloride formed by thermal decomposition of a chlorine-containing resin to sequester it, and then subjecting the polyalkylene terephthalate to methanolysis and recovering the starting monomer.

Also, Japanese Unexamined Patent Publication HEI No. 8-259728 proposes a process whereby a mixture of a chlorine-containing resin and polyester waste is hydrolyzed in the presence of an alkali compound and then terephthalic acid and EG are recovered, i.e., similarly, an alkali compound is added to sequester generated chlorine compounds.

While all of these processes achieve the object of recovering the target substances, they are associated with various drawbacks. Specifically, in cases where a chlorine-containing resin and its decomposition product are included as foreign materials, the chlorine compounds sequestered by the alkali compound must be removed, and the removal of the chlorine compounds requires the additional steps of distillation, washing and ion-exchange, thus complicating the process. In cases where a colored polyester is included as an foreign material, the high temperature treatment of the polyalkylene terephthalate decomposes part of the colorant and lowers the quality of the target substance. In cases where a polyolefin is included as an foreign material, melting treatment of the polyalkylene terephthalate together with its decomposition product makes it inevitable that the component to be recovered will be included in the polyolefin when it is removed from the thermal decomposition tank.

Japanese Unexamined Patent Publication HEI No. 11-21374 also proposes a process of hydrolyzing polyester waste in the presence of an alkali compound. However, since the decomposition is carried out in an alkaline aqueous system, this process has the drawback of a high reaction pressure.

Finally, Japanese Unexamined Patent Publication HEI No. 11-302208 proposes a process in which polyester waste is hydrolyzed in water-containing ethylene glycol in the presence of an alkali compound and the resulting sodium terephthalate is dissolved in a large amount of water and subjected to acid precipitation. According to this process, the presence of the ethylene glycol allows the reaction pressure to be lowered during the hydrolysis, but a drawback is encountered in that the acid precipitation produces a mineral acid salt in an amount almost equivalent to the terephthalic acid, and which is contained in the recovered terephthalic acid, or else the particle size of the produced terephthalic acid is reduced, leading to difficult handling of the powder during the polymerization process.

DISCLOSURE OF THE INVENTION

It is an object of the present invention to provide a process for recovery of dimethyl terephthalate and ethylene glycol from polyester waste (which may be either valuable or valueless substances) which contains polyethylene terephthalate as the major component along with foreign materials.

This object may be achieved by the following process according to the present invention.

The process of the present invention for separation and recovery of dimethyl terephthalate and ethylene glycol from polyester waste according to the invention is characterized in that a polyester waste containing polyethylene terephthalate as the major component along with foreign materials is successively subjected to the steps (a) to (f):

step (a) in which the polyester waste is mixed into ethylene glycol containing a polyester depolymerization catalyst, the resultant mixture is treated at a temperature of 175 to 190° C. under a pressure of 0.1 to 0.5 MPa, and, from solid foreign materials contained in the resulting reaction solution, a fraction of the solid foreign materials which have floated to the surface of the solution, is removed by means of a floatation separation method;

step (b) in which, from the solution fraction delivered from step (a), the residual solid foreign materials which are contained in the solution and have not floated to the surface in step (a), is removed by a solid/liquid separation method;

step (c) in which the residual solution fraction delivered from step (b) is distilled and concentrated, to recover the distilled ethylene glycol;

step (d) in which the distillation residue delivered from step (c) is mixed with a transesterification reaction catalyst and methanol to cause a transesterification reaction between the distillation residue and methanol to occur and to produce dimethyl terephthalate and ethylene glycol, the reaction mixture is subjected to recrystallization treatment and then to centrifugal separation to separate the reaction mixture into a dimethyl terephthalate cake and a mixture solution, and the cake is subjected to a distillation purification, to recover the distilled dimethyl terephthalate, having a high degree of purity;

step (e) in which the mixture solution delivered from step (d) is subjected to a distillation treatment to recover the distilled methanol, and step (f) in which the distillation residue delivered from step (e) is subjected to a distillation treatment to recover the distilled ethylene glycol.

In the separation and recovery process of the present invention, the depolymerization catalyst for step (a) preferably contains at least one metal compound selected from the group consisting of metal carbonates, metal carboxylates, metal oxides and metal alkoxides, and the amount of the catalyst is preferably controlled to 0.1 to 10% based on the weight of the polyester waste.

In the separation and recovery process of the present invention, the metal compound for the depolymerization catalyst preferably selected from the group consisting of sodium carbonate, sodium carboxylates, manganese acetate and zinc acetate.

In the separation and recovery process of the present invention, the amount of the ethylene glycol used in step (a) is preferably controlled to 0.5 to 20 times the weight of the polyester waste.

In the separation and recovery process of the present invention, the distilling and concentrating procedure in step (c) is preferably carried out under a pressure of from 1.33 kPa to 0.133 MPa.

In the separation and recovery process of the present invention, the foreign materials contained in the polyester waste may comprise at least one member selected from the group consisting of polyesters other than polyethylene terephthalate, or polyvinyl chloride, polyvinylidene chloride, polyolefins, polystyrene, acryl, rayon, acetate, polyvinyl alcohol, natural plant fibers, metals, pigments, oils, inorganic compounds, sand, paper, wood, glass, asbestos, carbon black and heat insulating materials.

In the separation and recovery process of the present invention, the polyesters other than polyethylene terephthalate which are contained as foreign materials in the polyester waste may comprise at least one member selected from the group consisting of copolymerized polyethylene terephthalates, polyethylene naphthalate, polytrimethylene terephthalate and polybutylene terephthalate.

In the separation and recovery process of the present invention, the polyolefins contained as foreign materials in the polyester waste may be polyethylene and/or polypropylene.

In the separation and recovery process of the present invention, the solid fraction which has floated to the solution surface in step (a) may contain a polyolefin and/or polystyrene.

In the separation and recovery process of the present invention, the solid foreign materials which are removed in step (b) may comprise at least one member selected from the group consisting of polyvinyl chloride, polyvinylidene chloride, unreacted polyester, acryl, rayon, acetate, polyvinyl alcohol, natural plant fibers, metals, inorganic compounds, sand, paper, wood, glass, asbestos and heat insulating materials.

In the separation and recovery process of the present invention, the ethylene glycol recovered in step (c) is preferably recirculated to step (a).

In the separation and recovery process of the present invention, the polyester waste may further comprise, as a foreign material other than polyethylene terephthalate, at least one member selected from the group consisting of polyamides, natural animal fibers, polycarbonates, polyurethanes, polylactic acid and dyes, and before step (a), a step (g) in which the polyester waste is mixed into ethylene glycol and treated at a temperature of 120 to 175° C. under a pressure of 0.1 to 0.5 MPa to prepare a solution, the undissolved solid fraction is separated from the solution and the separated solid fraction is fed to step (a).

The method for reutilization of recovered dimethyl terephthalate of the present invention comprises reutilizing dimethyl terephthalate recovered by the separation and recovery process of the present invention as a starting material for production of terephthalic acid.

The method for reutilization of recovered dimethyl terephthalate of the present invention comprises reutilizing dimethyl terephthalate recovered by the separation and recovery process of the present invention as a starting material for production of bis($\beta$-hydroxyethyl) terephthalate.

The method for reutilization of recovered dimethyl terephthalate of the present invention comprises utilizing dimethyl terephthalate recovered by the separation and recovery process of the present invention, as a starting material for production of polyester.

BEST MODE FOR CARRYING OUT THE INVENTION

Figure 1:
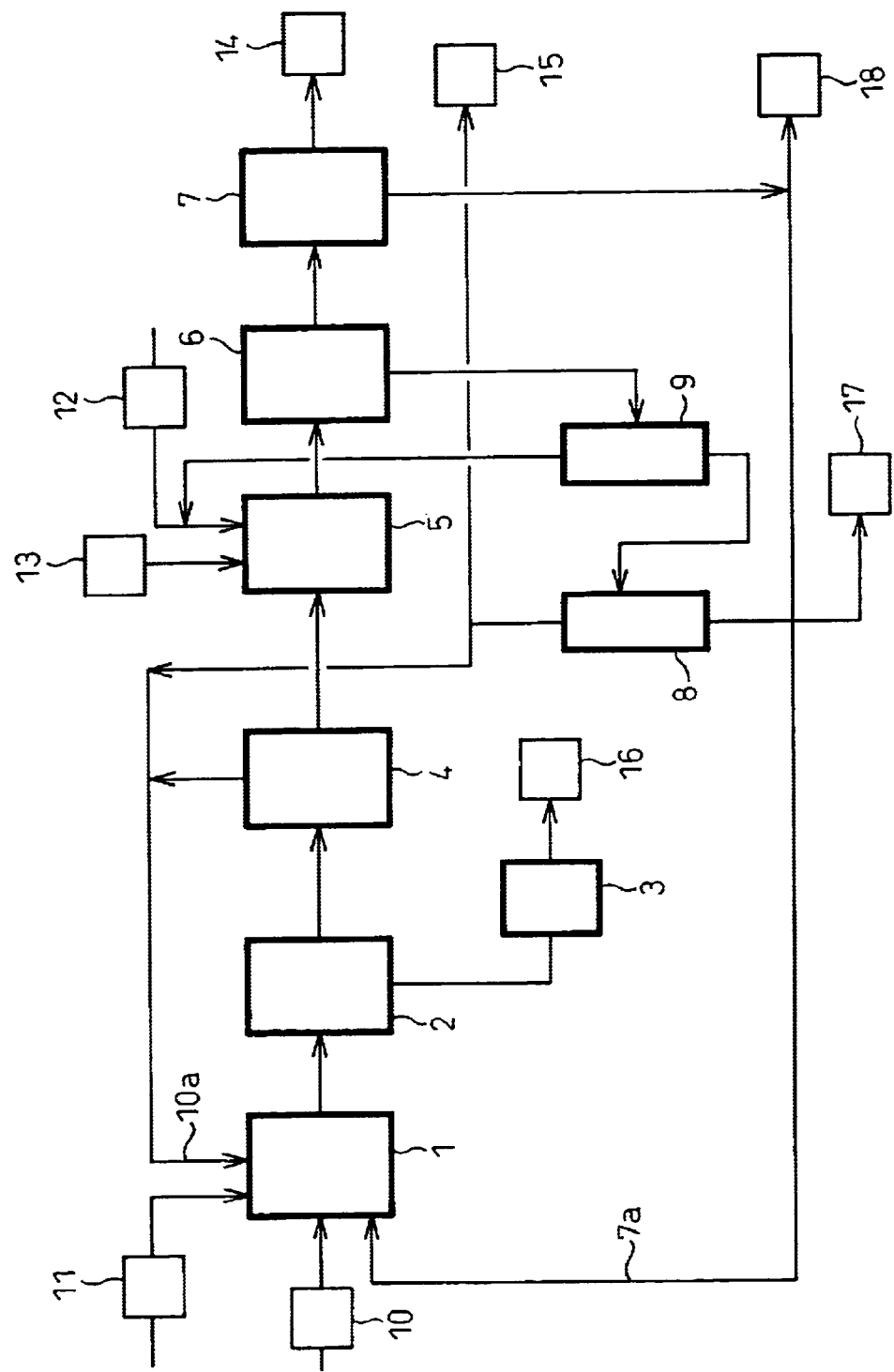
FIG. 1 is an illustration showing the steps for an embodiment of the process of the present invention as applied to polyester waste containing polychloride compounds.

According to the process of the invention, dimethyl terephthalate and ethylene glycol are separated and recovered from a polyester waste containing polyethylene terephthalate as the major component along with foreign materials. In the separation and recovery process of the present invention, polyester waste is successively subjected to the following steps (a) to (f):

step (a) wherein a polyester waste is mixed into ethylene glycol containing a polyester depolymerization catalyst, the resultant mixture is treated at a temperature of 175 to 190° C. under a pressure of 0.1 to 0.5 MPa, and, from the solid foreign materials contained in the resultant reaction solution, a fraction of the solid foreign materials which has floated to the surface of the solution, is removed by means of a floatation separation method, step (b) in which, from the solution fraction delivered from step (a), the residual solid foreign materials which are contained in the solution and have not floated to the station surface in step (a), is removed by a solid/liquid separation method;

step (c) in which the residual solution fraction delivered from step (b) is distilled and concentrated to recover the distilled ethylene glycol, step (d) in which the distillation residue delivered from step (c) is mixed with a transesterification reaction catalyst and methanol to cause a transesterification reaction between the residue and methanol to occur and to produce dimethyl terephthalate and ethylene glycol, the resultant reaction mixture is subjected to a recrystallization treatment and then to centrifugal separation to separate the reaction mixture into a dimethyl terephthalate cake and a mixture solution, and the cake is subjected to a distillation purification to recover the distilled dimethyl terephthalate, having a high degree of purity;

step (e) in which the mixture solution delivered from step (d) is subjected to a distillation treatment to recover the distilled methanol, and step (f) in which the distillation residue delivered from step (e) is subjected to a distillation treatment to recover the distilled ethylene glycol.

The major component of the polyester waste supplied to the process of the invention is polyethylene terephthalate, and the foreign materials comprise at least one member selected from the group consisting of polyesters other than polyethylene terephthalate, or polyvinyl chloride, polyvinylidene chloride, polyolefins, polystyrene, acryl, rayon, acetate, polyvinyl alcohol, natural plant fibers, metals, pigments, oils, inorganic compounds, sand, paper, wood, glass, asbestos, carbon black and heat insulating materials.

The polyesters other than polyethylene terephthalate which are contained as foreign materials in the polyester waste may comprise at least one member selected from the group consisting of copolymerized polyethylene terephthalate, polyethylene naphthalate, polytrimethylene terephthalate and polybutylene terephthalate.

The polyolefins to be contained as foreign materials in the polyester waste include polyethylene and/or polypropylene.

The natural plant fibers to be contained as foreign materials in the polyester waste include cotton and/or hemp.

Each of the aforementioned steps will be explained below.
Step (a)

In step (a), the polyester waste is treated in ethylene glycol containing a polyester depolymerization catalyst, at a temperature of 175 to 190° C. and preferably 180 to 185° C., under a pressure of 0.1 to 0.5 MPa and preferably 0.1 to 0.2 MPa, for depolymerization of the polyester.

When the treatment temperature in step (a) is below 175° C. under a pressure of 0.1 to 0.5 MPa, the necessary depolymerization time is lengthened and the production efficiency is reduced. When the treatment temperature exceeds 190° C., the foreign materials undergo notable thermal decomposition and the quality of the compound to be recovered is lowered. Also, a pressure of less than 0.1 MPa is inconvenient since it requires a pressure reduction apparatus which complicates the process, while a pressure of greater than 0.5 MPa is also inconvenient since the depolymerization reaction tank and accessory equipment must be suitable for high pressure, and removal of the reaction by-product water becomes difficult, creating an undesirable situation in terms of plant operation efficiency and safety.

The depolymerization catalyst used for step (a) preferably contains at least one metal compound selected from the group consisting of metal carbonates, metal carboxylates, metal oxides and metal alkoxides, and the depolymerization catalyst is preferably employed in an amount of 0.1 to 10% and more preferably 0.1 to 5% based on the weight of the polyester waste. Such depolymerization catalysts can accelerate depolymerization of the polyester and reduce the temperature required for depolymerization.

The metal compound usable for the depolymerization catalyst may be selected from among compounds of alkali metals, alkaline earth metals, titanium, manganese, cobalt, zinc, antimony, lead and cerium, and more preferably, the metal compound usable for the depolymerization catalyst is selected from the group consisting of sodium carbonate, sodium carboxylates, manganese acetate and zinc acetate.

The amount of the ethylene glycol used in step (a) is preferably 0.5 to 20 times and more preferably 1 to 5 times the weight of the polyester waste. By using the ethylene glycol in this weight ratio, it is possible to control variation in the time required for depolymerization depending on the geometry of the polyester waste, and thereby minimize the ethylene glycol purification cost.

While there are no particular restrictions on the depolymerization treatment time in step (a), it will usually be 1 to 10 hours under the conditions described above.

Incidentally, although it is possible to obtain the effect of a shortened melting time by combining procedures such as agitation of the melt vessel contents and circulation of the vessel solution with an external pump for temperature increase of the polyester waste and the catalyst between the polyester waste and ethylene glycol, excessive agitation and the like require extra power, and therefore it is sufficient to merely produce a flow of the solution in the vessel.

The reaction system may be a continuous reaction system or a batch reaction system.

Fine pulverization of the polyester waste will produce some effect of shortening of the melting time, but considering the extent of filtration leakage when extracting the foreign materials such as PVC as solids and the power required for pulverization, it is preferably cut or crushed to a 1 to 30 mm square size in the case of a molded article, to 10 to 50 mm cut fibers in the case of fibers, or to a 5 to 20 mm square size in the case of a film.

Once the depolymerization treatment of step (a) has been completed, the solid foreign materials, such as polyolefin, which has floated to the surface of the solution among the solid foreign materials contained in the resulting reaction solution is removed by means of a floatation separation method. The floatation matter separation method used here may be a conventional separation method, and for example, the floating foreign materials on the surface of the reaction solution may be withdrawn from or allowed to overflow over the depolymerization reaction vessel.

The solid portion which floats to the solution surface in step (a) contains a polyolefin and/or polystyrene.

After the floating portion which has floated to the surface of the reaction solution in step (a) has been removed, the remaining reaction solution is supplied to step (b).

In step (b), a solid/liquid separation method is employed to remove from the reaction solution the solid foreign materials (non-floating) which are contained therein. The solid foreign materials include one or more types from among chlorine-containing polymers (polyvinyl chloride (PVC), polyvinylidene chloride, etc.), unreacted polyester, acryl resin, rayon, acetate, polyvinyl alcohol, natural plant fibers, colorants, modified forms thereof, sand, dust and the like. There are no particular restrictions on the solid/liquid separation method, and there may be employed a filtration method, centrifugal separation method, precipitation method, etc. depending on the types and amounts of the solid foreing. materials.

The PVC obtained by the procedure of step (b) may be separated and recovered as a usable substance or as waste, but since ethylene glycol (EG) containing polyalkylene terephthalate waste will have adhered to the surface of the PVC obtained by solid/liquid separation, the surface is preferably washed with ethylene glycol before being supplied to step (a) in the case of recovery as a usable substance. The washing may be accomplished by charging the solid/liquid separated PVC into a vessel containing therein the ethylene glycol to be supplied to step (a), carrying out the agitate-washing and repeating the solid/liquid separation procedure.

Colorants included as foreign materials in the polyester waste are believed to exist in fine particle form in the alkylene glycol after depolymerization treatment of polyester waste and can be easily removed out of the system either by the filtration procedure described above or by a distillation procedure for DMT, alkylene glycols, methanol or bishydroxyalkyl terephthalates; such colorants will not be included in the product recovered by the process of the invention.

In the reaction solution obtained by the procedure of step (b), the polyester is depolymerized by ethylene glycol and converted to oligomers with 1–4 repeating units. The solution containing these oligomers is directly supplied to step (c). In step (c), the reaction solution portion is distilled and concentrated and the resultant distilled ethylene glycol is recovered.

There are no particular restrictions on the means for the distillation/concentration in step (c), and any conventional distillation/concentration apparatus, for reduced pressure continuous distillation, reduced pressure batch distillation or the like, may be used. Step (c) is carried out preferably at a temperature of 140 to 180° C. and more preferably 150 to 170° C.

The distillation/concentration procedure in step (c) may be carried out either under the ambient atmospheric pressure or under reduced pressure, but considering that the boiling point of ethylene glycol is 198° C., that the thermal decomposition of PVC considerablly occurs at a temperature of 195° C. or more and that the solution is contaminated with the fine particulate PVC leaks during the solid/liquid separation operation, the distillation/concentration pressure is preferably controlled to 1.33 to 100 kPa, and the reduced pressure distillation is preferably carried out under a pressure of 6.65 to 26.6 kPa. The concentration is preferably carried out to an extent such that the weight ratio of ethylene glycol in the distillation residue to the charged polyester waste is 0.5 to 2.0.

The ethylene glycol recovered in step (c) may be recirculated the step (a) and used in this step.

The residual fraction delivered as a distillation residue from step (c) is supplied to step (d), a transesterification reaction catalyst and methanol are added to the residue, a transesterification reaction between the residue and methanol is conducted to produce dimethyl terephthalate and ethylene glycol, the resultant reaction mixture is subjected to a recrystallization treatment and then to a centrifugal separation to separate the reaction mixture into a dimethyl terephthalate cake and a mixture solution, the cake is subjected to a distillation purification, and then the high-purity distilled dimethyl terephthalate is recovered.

In step (d), dimethyl terephthalate (DMT) may be obtained even if the transesterification reaction is carried out at a temperature of 65 to 85° C. but, as the DMT recovery yield is minimal when a large amount of ethylene glycol is present in the residue, the ethylene glycol is recovered first by step (c). It is therefore preferred, as mentioned above, for the concentration of ethylene glycol in the distillation residue delivered from step (c) to be 0.5 to 2.0 in terms of the weight ratio with respect to the charging weight of the polyester waste.

In the transesterification reaction of step (d), the methanol is preferably charged in an amount of 150 to 400 wt % based on the weight of the charged polyester waste, and the transesterification reaction catalyst is preferably charged simultaneously in an amount of 0.3 to 10 wt % based on the weight of the charged polyester waste. The pressure in the transesterification reaction vessel may be 0.1 to 0.3 MPa, and the transesterification reaction temperature is preferably 65 to 85° C.

The transesterification reaction is completed in 0.5 to 5 hours, and a slurry wherein solid dimethyl terephthalate (DMT) is dispersed in a mixed solution of methanol (MeOH) and ethylene glycol (EG) is obtained. A conventional solid/liquid separation apparatus may be employed as for recovery of the DMT from the slurry, but other methods may also be used.

Since a small amount of DMT is dissolved in the mixed solution of MeOH and EG, the slurry is cooled to 30 to 60° C. and then supplied to a solid/liquid separation apparatus. The CMT cake obtained by the solid/liquid separation procedure contains MeOH and EG as a mother liquor, and the cake is therefore mixed into fresh MeOH and agitated to reproduce a slurry, for washing of the DMT. The obtained slurry is then supplied again to a solid/liquid separation apparatus for separation into a DMT cake and a mother liquor consisting of MeOH.

The number of times this washing procedure is repeated will basically be established by the quality required for the recovered DMT, but the procedure will normally be carried out 2 to 4 times. The mother liquor MeOH may also be recirculated at each washing stage, as is conventional. The washing procedure may be carried out by a continuous system or a batch system.

The mixed solution of EG and MeOH separated from the DMT is then supplied to step (e). In step (e), the mixed solution of EG and MeOH includes DMT, the depolymerization catalyst and the transesterification reaction catalyst dissolved therein, and therefore in order to reuse the EG and MeOH for the process of the present invention it is necessary to separate and purify each. The purification procedure is preferably carried out by distillation, but there is no particular limitation to distillation. When it is carried out by distillation, MeOH having a low boiling point is distilled off in a front distillation column of step (e), and a solution function remaining in the bottom of the front distillation column is supplied to the next distillation column and then to step (f) for distilling off of the EG. In this distillation in step (f), since DMT dissolved in EG, catalyst and oligomers with 1 to 3 repeated units are present in the bottom of the distillation column, a portion of the solution in the bottom of the column may be delivered therefrom and returned to the depolymerization vessel (step (a)) in order to reduce the consumption of catalyst and improve the yield of the effective components.

In step (d), since trace amounts of solids such as dust and sand contained in the polyester waste may possibly be included in the recovered dimethyl terephthalate (DMT), it may be purified by distillation under reduced pressure if necessary, depending on the level of quality required for the DMT, and a portion of the solution remaining in the bottom of the distillation column by this purification procedure may be returned to the depolymerization vessel of step (a).

According to the process of the invention, when the polyester waste contains, as foreign materials other than polyethylene terephthalate, at least one member of additional foreign materials selected from the group consisting of polyamides, natural animal fibers, polycarbonates, polyurethanes, polylactic acid and dyes, step (a) may be preceded by a step (g) in which the polyester waste containing the above-mentioned foreign materials is mixed into ethylene glycol and the resultant mixture is heat-treated at a temperature of 120 to 175° C. under a pressure of 0.1 to 0.5 MPa to prepare a solution, a undissolved solid fraction is separated from the solution and supplying the separated solid fraction to step (a).

In step (g), the additional foreign materials are dissolved in ethylene glycol while the main polyethylene terephthalate component and the previously mentioned foreign materials are separated from the additional foreign materials as undissolved solid fraction. The treatment temperature in step (g) is 120 to 175° C., preferably 150 to 170° C. A treatment temperature of below 120° C. is inconvenient because the foreign materials other than polyethylene terephthalate may not thoroughly dissolve in the ethylene glycol, while a treatment temperature of above 175° C. is inconvenient because the foreign materials may undergo thermal decomposition and reduce the quality of the recovered DMT and EG. The treatment pressure is 0.1 to 0.5 MPa, and preferably near the ambient atmospheric pressure. A treatment pressure of less than 0.1 MPa is inconvenient because it requires a pressure reduction apparatus which may cause the process to be complicated, while a pressure of greater than 0.5 MPa is also inconvenient as the depolymerization reaction vessel and accessory equipment must be resistant to high pressure, and removal of the reaction by-product water becomes difficult, often creating an undesirable situation in terms of plant operation efficiency and safety. The treatment time may be set as appropriate, but is usually preferred to be 0.5 to 5 hours and more preferably 1 to 3 hours.

The dimethyl terephthalate recovered in the separation and recovery process of the present invention may be used as a starting material for production of terephthalic acid.

The dimethyl terephthalate recovered in the separation and recovery process of the present invention may also be used as a starting material for production of bis(β-hydroxyethyl) terephthalate.

The dimethyl terephthalate recovered in the separation and recovery process of the present invention may also be used as a starting material for production of polyester.

The separation and recovery process of the present invention will now be explained in detail by referring to FIG. 1 which shows an embodiment of the separation and recovery process of the invention.

In FIG. 1, a polyester waste containing pulverized polyalkylene terephthalates and polyvinyl chloride (PVC) supplied from a supply source 11, a depolymerization catalyst from supplied from a supply tank 10 and ethylene glycol supplied from a supply line 10a are simultaneously charged into a depolymerization vessel 1, and the polyester waste is depolymerized in the depolymerization vessel 1.

The depolymerized mixture is fed to a solid/liquid separation apparatus 2.

The PVC which has not been dissolve in the EG in the depolymerization tank 1 is separated in the solid/liquid separation apparatus 2 and delivered to outside of the system as a solid material. The solid material is further washed with EG in a washing tank 3, the substances adhering to the surface of the solid matter are recirculated to the depolymerization vessel 1 if necessary, and the solid material 16 composed of PVC is separated and removed. Here, the residence time of the polyester waste in the depolymerization vessel 1 may be 1 to 10 hours and the internal temperature of the vessel 1 175 to 190° C.

Then, the polyester waste which has been delivered from the depolymerization reaction is fed into a distillation/concentration vessel 4 and the EG is distilled off until the charging weight ratio of the EG and polyester waste is 0.5 to 2. The distilled EG may be recirculated to the depolymerization vessel 1.

The concentrated solution of the depolymerized polyester waste is then supplied to a transesterified reaction vessel 5, to which a transesterification reaction catalyst is supplied from its supply source 13 and MeOH is supplied from its supply source 12, to convert the depolymerized polyester waste solution into DMT and alkylene glycol. In this case, the transesterification vessel preferably has a capacity sufficient carrying out the transesterification reaction at a temperature of 65 to 85° C., under a pressure of 0.1 to 0.3 MPa for a residence time of 0.5 to 5 hours.

The produced mixture of DMT and alkylene glycol is cooled together with an excess amount of MeOH, and the cooled mixture then supplied to a solid/liquid separation apparatus 6 for separation of the DMT cake from the mixed liquid of alkylene glycol with MeOH. The separated DMT cake contains MeOH as a mother liquor, and it is therefore converted to slurry again in MeOH and again subjected to the solid/liquid separation. The second slurry-preparing step and solid/liquid separation step for the DMT cake are not shown in FIG. 1.

The twice washed DMT cake is fed into a DMT distillation column 7 and the resultant refined DMT 14 is recovered. A portion of the residual liquid fraction in the bottom of the distillation column 7 is returned to the depolymerization vessel 1 through a line 7a, and the remainder is discharged to the outside of the system 18.

Meanwhile, the mixed liquid of ethylene glycol with MeOH which were separated in the solid/liquid separation apparatus 6 is fed into a MeOH distillation column 9 and an EG distillation column 8, and the MeOH and EG are distilled off. The distilled off MeOH may be used as a part of the MeOH to be supplied to the transesterification reaction vessel 5.

Also, the residual liquid fraction in the bottom of the MeOH distillation column 9 is fed into the EG distillation column 8, to distill EG. A portion of the distilled EG is used as a portion of EG to be supplied to the depolymerization vessel 1 through a line 10a, while the remaining EG is recovered and delivered to the outside of the system 15.

A portion of the residual liquid fraction in the EG distillation column 8 is returned to the depolymerization vessel 1 and the remainder is discharged as a waste to the outside of the system 17.

The procedure described above allows easy recovery of DMT and ethylene glycol as effective components from polyalkylene terephthalate waste containing PVC.

The separation and recovery process of the invention will now be explained in detail by referring to FIG. 2 which shows another embodiment of the separation and recovery process of the invention.

First, a pulverized polyolefin-containing polyester waste supplied from a supply source 29, a depolymerization catalyst supplied from a supply tank 30 and ethylene glycol supplied from a supply line 21a are charged into a depolymerization vessel 21, and the polyester waste is depolymerized therein.

The polyolefin floating on the solution surface without dissolving in the ethylene glycol in the depolymerization vessel 21 is removed, and the residue is fed into a distillation/concentration vessel 22. The residence time of the polyester waste in the depolymerization vessel may be about 4 hours and the internal temperature of the vessel may be approximately 185° C. The floating polyolefin 37 is removed.

Then, a reaction liquid of the resultant depolymerized polyester waste is fed into the distillation/concentration tank 22 while the charging weight ratio of the ethylene glycol to polyester waste is controlled to 1:1, the ethylene glycol is distilled and the distilled off ethylene glycol is recirculated to the. depolymerization vessel 21.

The resultant concentrated solution of the decopolymerized polyester waste is then fed into a transesterified reaction vessel 23, to which a transesterification reaction catalyst is also fed from its supply source 31 and MeOH is fed from its supply source 32, to convert the depolymerized polyester waste into DMT and ethylene glycol. Here, the transesterified reaction vessel preferably has a capacity sufficient to carry out the transesterification reaction a temperature of approximately 75° C., under ambient atmospheric pressure for a residence time of 2 hours.

The produced DMT and ethylene glycol mixture are cooled together with an excess amount of MeOH, and the cooled mixture is then fed into a solid/liquid separation apparatus 25 for separation of the DMT cake from a mixed liquid of alkylene glycol with MeOH. The DMT cake is converted to slurry again in MeOH and washed and again subjected to a solid/liquid separation (not shown).

The twice washed DMT cake is fed into a DMT distillation column 26 and the resultant refined DMT 53 is recovered. The residual liquid fraction 35 in the bottom of the distillation column 26 is discharged from the system.

Separately, the mixed liquid of ethylene glycol and MeOH separated in the solid/liquid separation apparatus 25 is fed into a MeOH distillation column 27, and the MeOH is removed by distillation. The distilled MeOH may be used as portion of the MeOH to be supplied to the transesterification reaction vessel 23.

Also, the residual liquid fraction in the bottom of the MeOH distillation column 27 is fed into an ethylene glycol distillation column 28, and the ethylene glycol is distilled. A portion of the distilled ethylene glycol is used as a portion of ethylene glycol to be supplied to the depolymerization vessel 21, while the remaining EG is removed from the system as recovered EG 34. In addition, the residual liquid fraction 36 in the ethylene glycol distillation column 28 is discharged as waste from the system as waste.

The procedure described above allows easy recovery of DMT and ethylene glycol as effective components from polyolefin-containing polyester waste.

Figure 2:
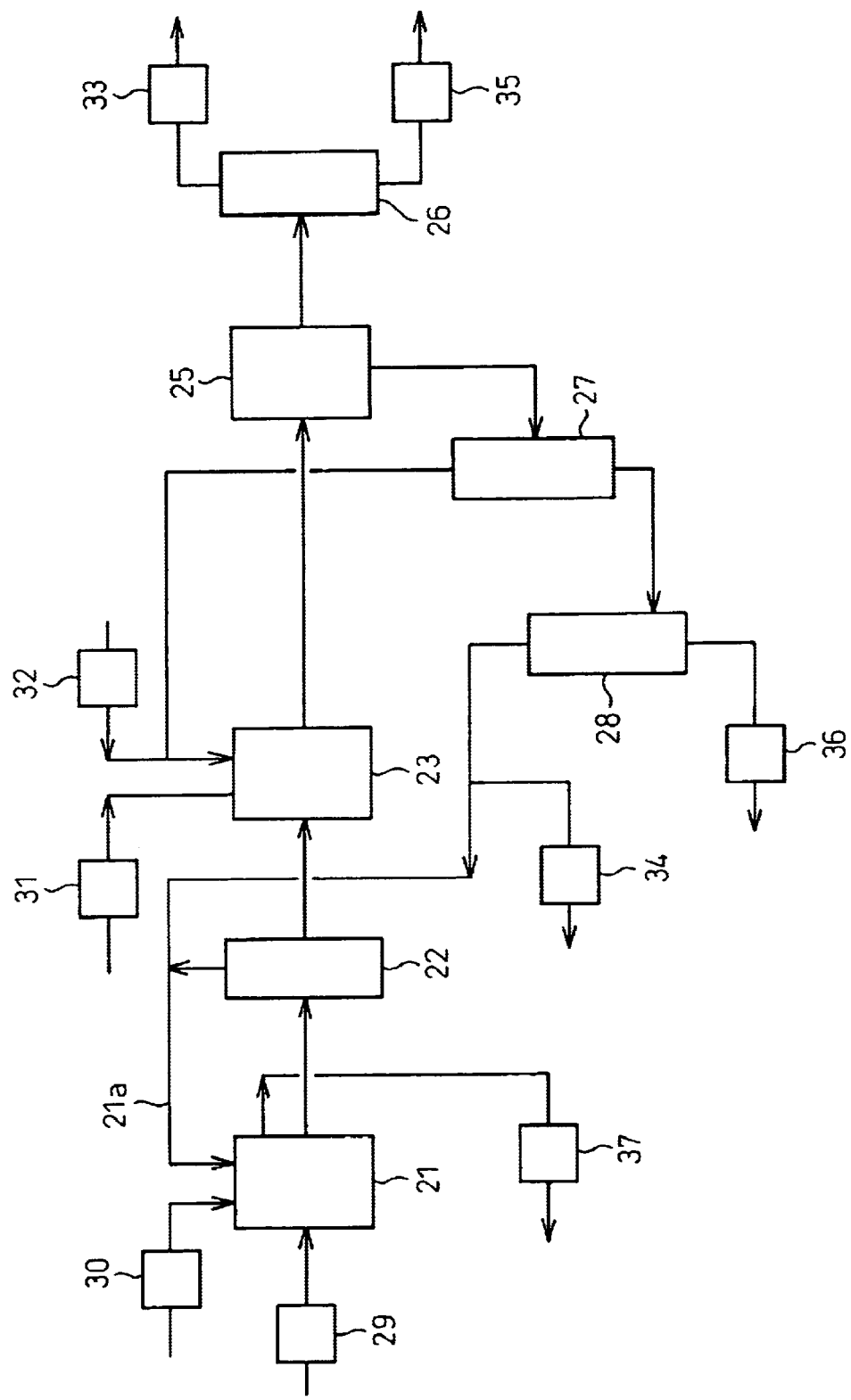
FIG. 2 is an illustration showing the steps for an embodiment of the process of the present invention as applied to polyester waste containing polyolefins.

In each of the separation and recovery apparatuses shown in FIGS. 1 and 2, when the polyester waste contains, as foreign materials other than polyethylene terephthalate, at least one additional foreign material selected from the group consisting of polyamides, natural animal fibers, polycarbonates, polyurethanes, polylactic acid and dyes, an apparatus may be provided, between the polyester waste supply source 10 or 29 and the depolymerization vessel 1 or 21, with an apparatus removal of the additional foreign materials in the form of an ethylene glycol solution.

EXAMPLES

The present invention will be further explained in detail by way of examples which are not intended to limit the scope of the present invention any way.

The following measurements were carried out for Examples 1–8 and Comparative Examples 1–2.

(1) Contents (%) of DMT, MHET and BHET:

The DMT content after depolymerization, the DMT content before and after distillation, and contents of the monohydroxyethylmethyl terephthalate (hereinafter also abbreviated as "MHET") and bishydroxyethyl terephthalate (hereinafter also abbreviated as "BHET") contained in the residual liquid fraction in distillation column were measured by gas chromatography (HP-5890 by Hewlett-Packard, capillary column: TC-1701 by G.L. Science).

(2) EG content (%):

The EG content after depolymerization and the EG content in the distillation liquid before and after distillation were measured by gas chromatography (GC-7A by Shimazu Laboratories, packing column filler: Polyalkylene Glycol-6000 by G.L. Science).

(3) weight-average molecular weight of oligomer:

A partially depolymerized PET waste in a melt state was subjected, as a sample, to a liquid chromatography (L-4000 by Hitachi Laboratories) using tetrahydrofuran as the mobile phase and a mixed solvent consisting of hexafluoro-2-propanol and chloroform as a solvent for the sample. The weight average molecular weight of the sample was determined with reference to a calibration curve prepared using standard polystyrene.

(4) Content of chlorine contained in DMT:

Recovered DMT was dissolved in MeOH, and the chlorine concentration of the solution was determined with a chlorine-sulfur analyzer/whole organic halogen analyzer (TOX-100 by Mitsubishi Chemical Corp.), with reference to the premeasured chlorine content of a mixture used as the standard.

Example 1

After placing 360 parts by weight of EG in a separable flask, 5 parts by weight of a soft vinyl chloride hose (30000 Vinyl Hose, General Research Catalog, Iuchi Seieido Co., Ltd.) and 5 parts by weight of a hard vinyl chloride pipe (MS4000 Hard Transparent Vinyl Chloride Pipe by Asahi Laboratories Co., Ltd.) cut into rings, 45 parts by weight of 100% polyethylene terephthalate (hereinafter also abbreviated as "PET") fiber waste cut into a 3 to 5 cm lengths, 45 parts by weight of PET bottle cut into 3 to 10 mm squares and 2.7 parts by weight of sodium carbonate (as a depolymerization catalyst), were further placed in the flask, and the resultant mixture was kept at 183° C. for 4 ½ hours with stirring.

The above-mentioned EG treatment liquid was fed into a filtration apparatus surrounded by a heating jacket at 170° C. and equipped with a 100 mesh wire net as a filter, and heat-filtrated therethrough. The PVC remaining on the filter was washed with 90 parts by weight of EG heated to 170° C., and the washing liquid was received by a separate container.

The EG solution delivered from the heat-filtration was concentrated by distillation under reduced pressure of 6.65 kPa, and 270 parts by weight of EG was recovered as a distilled fraction.

Into the concentrated liquid, a transesterification reaction catalyst consisting of 2.7 parts by weight of sodium carbonate and 180 parts by weight of MeOH was mixed. The resultant mixture was kept at a temperature of 75° C. for 1 hour under the ambient atmospheric pressure with stirring, to carry out a transesterification reaction.

The resultant mixture of DMT, with EG and MeOH was cooled to 40° C. and filtered through a glass 3G-4 filter. The DMT collected on the filter was mixed into 180 parts by weight of MeOH, and the resulting mixture was stirred and washed at 40° C. and filtered again through a glass filter. The above-mentioned procedure was repeated twice.

The DMT collected on the filter was charged into a distillation apparatus, and distilled under a reduced pressure of 6.65 kPa, to recover 75 parts by weight of DMT as a distilled fraction. Based on the weight of the charged PET waste, the DMT recovery yield was 83 wt % and the EG recovery yield was 71 wt %. The chlorine in the distilled DMT fraction was measured with a trace chlorine analyzer but was below the detectable limit.

Examples 2–6 and Comparative Example 1

In each of Examples 2–6 and Comparative Example 1, a polyester waste was separated and recovered in the same manner as in Example 1, except that the type and amount of the depolymerization catalyst, and depolymerization temperature in Example 1 were changed as shown in Table 1 in order to investigate the effects thereof on the depolymerization time. The results are shown in Table 1.

TABLE 1

| | Catalyst type | Catalyst weight (wt %) (*1) | Depolymerization temperature (° C.) | Depolymerization time (Hr) |
|---|---|---|---|---|
| Example 2 | Sodium carbonate | 3 | 180 | 6.5 |
| Example 3 | Sodium carbonate | 1 | 183 | 5.5 |
| Example 4 | Manganese acetate | 3 | 183 | 7.0 |
| Example 5 | Zinc acetate | 3 | 185 | 4.5 |
| Example 6 | Sodium carbonate + zinc acetate | 6(3 + 3) | 185 | 3.8 |
| Comp. Ex. 1 | No catalyst | 0 | 185 | No reaction |

*1: Weight ratio of catalyst to PET contained in the polyester waste used

Comparative Example 2

The same separation and recovery procedure as in Example 1 was carried out, except that the depolymerization temperature was changed to 230° C., and the chlorine content of the recovered DMT was measured to be 210 ppm.

Example 7

The same separation and recovery procedure as in Example 1 was carried out, except that in the concentration of the depolymerized PET-containing EG liquid the EG was distilled until the EG/PET weight ratio was reduced to 0.2 based on the charged weight. The DMT was recovered at a yield of 55% based on the weight of the charged waste.

Example 8

The same separation and recovery procedure as in Example 1 was carried out, except that the EG was distilled off until the EG/PET weight ratio was reduced to 3 based on the charged waste weight. The DMT was collected at a yield of 78%.

Examples 1–8 confirmed that the process of the invention conveniently can yield DMT and EG from the polyester waste containing PVC.

The following tests were conducted in Examples 9–11 and Comparative Examples 3–5.

(1) Chlorine content in DMT (ppm):

Recovered DMT was dissolved in MeOH, and the chlorine concentration was determined with a chlorine-sulfur analyzer/whole organic halogen analyzer (TOX-100 by Mitsubishi Chemical Corp.), using the premeasured chlorine content of a mixture prepared, as the standard.

(2) Nitrogen content of ethylene glycol (ppm):

Recovered ethylene glycol was diluted with MeOH and the nitrogen concentration of the ethylene glycol was determined with a trace nitrogen analyzer (TN05 by Mitsubishi Chemical Corp.), using the premeasured nitrogen content of a mixture prepared as the standard.

Example 9

After placing 400 parts by weight of EG into a separable flask, 50 parts by weight of clear polyethylene terephthalate bottles cut into 3 to 10 mm squares, 40 parts by weight of green PET bottles cut into 3 to 10 mm squares and 3 parts by weight of sodium carbonate were further placed in the flask, and the temperature of the resultant mixture was raised to 185° C. while stirring the mixture at a stirring speed of 100 rpm. After maintaining the mixture under the above-mentioned conditions for 4 hours, the PET was dissolved and depolymerization was completed.

The depolymerization solution was filtered through a filtration apparatus heated on the periphery thereof and equipped with a 100 mesh wire netting as a filter. A trace amount of sandy solid materials, believed to have adhered to the bottles, remained on the filter.

The depolymerization liquid delivered from the filtration was concentrated by distillation under reduced pressure of 6.65 kPa, and 300 parts by weight of EG was recovered as a distilled fraction.

Into the concentrated liquid, 3 parts by weight of sodium carbonate as a transesterification reaction catalyst and 200 parts by weight of MeOH were mixed. The liquid was kept at a temperature of 75° C. for 2 hours under an ambient atmospheric pressure while stirring the mixture at a stirring speed of 100 rpm, to carry out a transesterification reaction.

The mixture of DMT with EG and MeOH was cooled to 40° C. and filtered through a glass 3G-4 filter. The DMT collected on the filter was mixed into 180 parts by weight of MeOH, and the resulting mixture was heat-stirred at 40° C., washed and filtered again through a glass filter while being heated. The filtration was repeated twice.

The DMT collected on the filter was charged into a distillation apparatus, and distilled under a reduced pressure of 6.65 kPa DMT was obtained as a distilled fraction. The DMT was recovered at a yield of 76 parts by weight. The amount of the residual DMT contained in the distillation liquid residue was measured to be 7 parts by weight, and the reaction yield of DMT was 91 wt % based on the charged polyester waste.

The content of nitrogen in the distilled DMT was measured with a total nitrogen analyzer and was below the detectable limit. The content of chlorine in the distilled DMT was measured by a fluorescent X-ray analysis, and was also below the detectable limit. After esterification reaction, the reaction mixture was subjected to a solid/liquid separation, the resultant filtrate liquid was subjected to a distillation for MeOH and EG, and the contents of nitrogen and chlorine contained in the MeOH and EG distillation product were measured with a whole nitrogen meter and trace chlorine analyzer, and were both below the detectable limit. The measurement results are shown in Table 2.

Example 10

The same separation and recovery procedure as in Example 9 was carried out, except that blue PET bottles were employed in place of the green PET bottles of Example 9. The results for the chlorine content of the recovered DMT and the nitrogen content of the recovered EG are shown in Table 2.

Example 11

The same separation and recovery procedure as in Example 9 was carried out, except that manganese acetate was used as the depolymerization catalyst instead of the sodium carbonate of Example 9. The PET was dissolved and depolymerization of PET was completed by 6 ½ hours. The measurement results for the chlorine content of the recovered DMT and the nitrogen content of the recovered EG are shown in Table 2.

Comparative Example 3

The same separation and recovery procedure as in Example 9 was carried out, except that the green PET bottle of Example 9 was replaced by clear PET bottles in the same amount as in Example 9. The measurement results for the chlorine content of the recovered DMT and the nitrogen content of the recovered EG are shown in Table 2.

Comparative Example 4

The same separation and recovery procedure of Example 9 was carried out, except that no sodium carbonate was employed as a depolymerization catalyst. The PET did not undergo depolymerization reaction, and experienced no change. The measurement results are shown in Table 2.

Comparative Example 5

The same separation and recovery procedure as in Example 9 was carried out, except that the temperature at which the depolymerization mixture was stirred and maintained in Example 9 was changed to 220° C. The dissolution and depolymerization of PET were completed by 2 hours and 15 minutes. The measurement results for the chlorine content of the recovered DMT and the nitrogen content of the recovered EG are shown in Table 2.

TABLE 2

| | Type of starting material | | | Recovered DMT | Recovered EG |
|---|---|---|---|---|---|
| | Colorless | Green bottle | Blue bottle | Cl concentration | N concentration |
| Example 9 | ○ | ○ | — | <1 ppm | <1 ppm |
| Example 10 | ○ | — | ○ | <1 ppm | <1 ppm |
| Example 11 | ○ | ○ | — | <1 ppm | <1 ppm |
| Comp. Ex. 3 | ○ | — | — | <1 ppm | <1 ppm |
| Comp. Ex. 4 | ○ | — | — | No reaction | |
| Comp. Ex. 5 | ○ | ○ | — | 3 ppm | 11 ppm |

The "○" symbols in Table 2 indicate that the starting material was charged for the process.

In Examples 9–11, it was confirmed that the process of the present invention allows convenient separation and recovery of clear dimethyl terephthalate and ethylene glycol as effective components from polyester waste containing colored polyester.

The following tests were conducted in Examples 12–16 and Comparative Examples 6–8.

(1) Content of olefins in the recovered DMT (ppm):

Recovered DMT was dissolved in chloroform and filtered through a filter paper sheet (GA100 by ADVANTEC), and the olefin content was determined from the difference in the weight of the paper sheet between before and after the filtration procedure.

(2) Content of olefins in the recovered ethylene glycol (ppm):

The recovered ethylene glycol was diluted with MeOH and filtered through a filter paper sheet (GA100 by ADVANTEC), and the olefin content was determined from the difference in the weight of the paper sheet between before and after the filtration procedure.

(3) Content of chlorine in the recovered DMT (ppm):

Recovered DMT was dissolved in MeOH, and the chlorine concentration was determined with a chlorine-sulfur analyzer/whole organic halogen analyzer (TOX-100 by Mitsubishi Chemical Corp.), using the premeasured chlorine content of a mixture used as the standard.

(4) Content of nitrogen in the recovered ethylene glycol (ppm):

Recovered ethylene glycol was diluted with MeOH and the nitrogen concentration in the ethylene glycol was determined with a trace nitrogen analyzer (TN05 by Mitsubishi Chemical Corp.), using the premeasured nitrogen content of a mixture used as the standard.

Example 12

After charging 400 parts by weight of EG into a separable flask, 10 parts by weight of polyethylene (Aldrich Co. Catalog No.18, 190-0; average molecular weight: 125,000) as a polyolefin, 90 parts by weight of clear polyethylene terephthalate bottles (cut into 3 to 10 mm squares) and 3 parts by weight of sodium carbonate were further placed in the flask and the temperature of the mixture in the flask was raised to 185° C. while stirring the mixture at a stirring speed of 100 rpm. After maintaining the mixture under the above-mentioned conditions for 4 hours, the dissolution and depolymerization of PET was completed.

After the polyethylene floating on the depolymerization liquid surface was scooped off with a metal wire net the depolymerization liquid was filtered through a filtration apparatus heated at the periphery thereof and equipped with a 100 mesh wire net as a filter. A trace amount of sandy solid matter, which is believed to have adhered to the bottles was, retained on the filter.

The depolymerization liquid obtained by the filtration was concentrated by distillation under a reduced pressure of 6.65 kPa, and 300 parts by weight of EG was recovered as a distilled fraction.

Into the concentrated liquid, 3 parts by weight of sodium carbonate as a transesterification reaction catalyst and 200 parts by weight of MeOH were mixed. The liquid mixture was kept at a temperature of 75° C. for 1 hour under the ambient atmospheric pressure while stirring the mixture at a speed of 100 rpm, for the 15 transesterification reaction.

The resultant mixture of DMT, with EG and MeOH was cooled to 40° C. and filtered through a glass 3G-4 filter.

The DMT collected on the filter was mixed into 180 parts by weight of MeOH, and the resultant mixture was heated 20 to 40° C. and then stirred, washed and filtered again through a glass filter. This procedure was repeated twice.

The DMT collected on the filter was charged into a distillation apparatus, and was distilled under a reduced 25 pressure of 6.65 MPa. The distilled DMT was recovered as a distilled fraction and was obtained at a yield of 78 parts by weight. The amount of DMT remaining in the distillation column was measured to be 6 parts by weight, and the DMT yield was 92 wt % based on the weight of the polyester waste. No polyolefin was present in the recovered DMT or the recovered EG. The measurement results are shown in Table 3.

Example 13

The same separation and recovery procedure as in Example 12 was carried out, except that polypropylene (Aldrich Co. Catalog No.18, 238-9; average molecular weight: 250,000) was mixed as a polyolefin into the polyester waste in Example 12. No polyolefin was present in the recovered DMT or the recovered EG. The measurement results are shown in Table 3.

Example 14

The same separation and recovery procedure of Example 12 was carried out, except that 5 parts by weight of polyethylene and 5 parts by weight of polypropylene were mixed as polyolefins into the polyester waste in Example 12. No polyolefin was found in the recovered DMT or the recovered EG. The measurement results are shown in Table 3.

Example 15

The same separation and recovery procedure as in Example 12 was carried out, except that manganese acetate was used instead of sodium carbonate as a depolymerization catalyst. The dissolution and depolymerization of PET were completed by 6 ½ hours. No polyolefin was found in the recovered DMT or the recovered EG. The measurement results are shown in Table 3.

Example 16

The same separation and recovery procedure as in Example 12 was carried out, except that 5 parts by weight of polyethylene, 2 parts by weight of polyethylene labels and 3 parts by weight of polyethylene caps were charged as polyolefins, and the temperature at which the depolymerization mixture was stirred and maintained was changed to 185° C. The dissolution and depolymerization of PET were completed by 4 hours. No polyolefin was found in the recovered DHT and the recovered EG.

The nitrogen and chlorine contents of the recovered DMT and the recovered EG were measured with a whole nitrogen meter and trace chlorine analyzer, and were both below the detectable limit. The measurement results of the chlorine content of the recovered DMT and the nitrogen content of the recovered EG are shown in Table 3.

Comparative Example 6

The same separation and recovery procedure as in Example 12 was carried out, except that the polyolefin used in Example 12 was replaced by clear PET. The measurement results for the chlorine content of the recovered DMT and the nitrogen content of the recovered EG are shown in Table 3.

Comparative Example 7

The same separation and recovery procedure as in Example 13 was carried out, except that no sodium carbonate was charged as a depolymerization catalyst. The PET did not undergo a reaction change.

Comparative Example 8

The same separation and recovery procedure as in Example 16 was carried out, except that the temperature at which the depolymerization mixture was stirred and maintained in Example 16 was changed to 220° C. The dissolution and depolymerization of PET were completed in 2 hours and 15 minutes. The measurement results for the chlorine content of the recovered DMT and the nitrogen content of the recovered EG are shown in Table 3.

TABLE 3

|  | Type of starting material | | | | | Recovered DMT Cl concentration | Recovered EG N concentration | Recovered DMT, EG Polyolefin |
| --- | --- | --- | --- | --- | --- | --- | --- | --- |
|  | Clear bottle | PE | PP | Labels | Cap |  |  |  |
| Example 12 | ○ | ○ | — | — | — | 0 ppm | 0 ppm | none |
| Example 13 | ○ | — | ○ | — | — | 0 ppm | 0 ppm | none |
| Example 14 | ○ | ○ | ○ | — | — | 0 ppm | 0 ppm | none |
| Example 15 | ○ | ○ | — | — | — | 0 ppm | 0 ppm | none |
| Example 16 | ○ | ○ | — | ○ | ○ | 0 ppm | 0 ppm | none |
| Comp. Ex. 6 | ○ | — | — | — | — | <1 ppm | <1 ppm | — |
| Comp. Ex. 7 | ○ | ○ | — | — | — | No reaction | | — |
| Comp. Ex. 8 | ○ | ○ | — | ○ | ○ | 14 ppm | 18 ppm | none |

The "○" symbols in Table 3 indicate that the starting material was charged.

In Examples 12–16 it was confirmed that the process of the present invention allows convenient recovery of bishydroxyethylene terephthalate and/or dimethyl terephthalate and ethylene glycol as effective components from polyolefin-containing polyester waste.

What is claimed is:

1. A process for separation and recovery of dimethyl terephthalate and ethylene glycol from polyester waste characterized in that a polyester waste containing polyethylene terephthalate as the major component along with foreign material is successively subjected to the following steps (a) to (f):

step (a) in which said polyester waste is mixed into ethylene glycol containing a polyester depolymerization catalyst, the resultant mixture is treated at a temperature of 175 to 190° C. under a pressure of 0.1 to 0.5 MPa, and, from solid foreign materials contained in the resulting reaction solution, a fraction of the solid foreign materials which have floated to the surface of said solution, is removed by means of a floatation separation method;

step (b) in which, from the solution fraction delivered from step (a), the residual solid foreign materials which are contained in the solution and have not floated to the solution surface in step (a) is removed, by a solid/liquid separation method;

step (c) in which the residual solution fraction delivered from step (b) is distilled and concentrated to recover the distilled ethylene glycol;

step (d) in which the distillation residue delivered from the step (c) is mixed with a transesterification reaction catalyst and methanol to cause a transesterification reaction between said distillation residue and methanol to occur to produce dimethyl terephthalate and ethylene glycol, the resultant reaction mixture is subjected to recrystallization treatment and then to centrifugal separation to separate the reaction mixture into a dimethyl terephthalate cake and a mixture solution, and said cake is subjected to a distillation purification, to recover the distilled dimethyl terephthalate, having a high degree of purity;

step (e) in which said mixture solution delivered from step (d) is subjected to a distillation treatment to recover the distilled methanol, and step (f) in which the distillation residue delivered through step (e) is subjected to a distillation treatment to recover the distilled ethylene glycol.

2. The separation and recovery process of claim 1, wherein the depolymerization catalyst for step (a) contains at least one metal compound selected from the group consisting of metal carbonates, metal carboxylates, metal oxides and metal alkoxides, and the amount of the catalyst is controlled to 0.1 to 10% based on the weight of said polyester waste.

3. The separation and recovery process of claim 2, wherein the metal compound for said depolymerization catalyst is selected from the group consisting of sodium carbonate, sodium carboxylates, manganese acetate and zinc acetate.

4. The separation and recovery process of claim 1, wherein the amount of the ethylene glycol for step (a) is controlled to 0.5 to 20 times the weight of said polyester waste.

5. The separation and recovery process of claim 1, wherein the distilling and concentrating procedure in step (c) is carried out under a pressure of from 1.33 kPa to 0.133 MPa.

6. The separation and recovery process of claim 1, wherein the foreign materials contained in said polyester waste comprise at least one member selected from the group consisting of polyesters other than polyethylene terephthalate, polyvinyl chloride, polyvinylidene chloride, polyolefins, polystyrene, acryl, rayon, acetate, polyvinyl alcohol, natural plant fibers, metals, pigments, oils, inorganic compounds, sand, paper, wood, glass, asbestos, carbon black and heat insulating materials.

7. The separation and recovery process of claim 6, wherein the polyesters other than polyethylene terephthalate which are contained as foreign materials in said polyester waste comprise at least one member selected from the group consisting of copolymerized polyethylene terephthalates, polyethylene naphthalate, polytrimethylene terephthalate and polybutylene terephthalate.

8. The separation and recovery process of claim 6, wherein the polyolefins contained as foreign materials in said polyester waste are polyethylene and/or polypropylene.

9. The separation and recovery process of claim 6, wherein the solid fraction which has floated to the solution surface in step (a) contains a polyolefin and/or polystyrene.

10. The separation and recovery process of claim 6, wherein the solid foreign material which is removed in step (b) comprises at least one member selected from the group consisting of polyvinyl chloride, polyvinylidene chloride, unreacted polyester, acryl, rayon, acetate, polyvinyl alcohol, natural plant fibers, metals, inorganic compounds, sand, paper, wood, glass, asbestos and heat insulating materials.

11. The separation and recovery process of claim 1, wherein the ethylene glycol recovered in step (c) is recirculated to step (a).

12. The separation and recovery process of claim 1, wherein said polyester waste further comprises, as a foreign material other than polyethylene terephthalate, at least one member selected from the group consisting of polyamides, natural animal fibers, polycarbonates, polyurethanes, polylactic acid and dyes, and before step (a), a step (g) in which the polyester waste is mixed into ethylene glycol and treated at a temperature of 120 to 175° C. under a pressure of 0.1 to 0.5 MPa to prepare a solution, the undissolved solid fraction is separated from said solution and the separated solid fraction is fed to step (a).

13. A method for reutilization of recovered dimethyl terephthalate, comprising utilizing dimethyl terephthalate recovered by the separation and recovery process as claimed in any one of claims 1 to 12, as a starting material for production of terephthalic acid.

14. A method for reutilization of recovered dimethyl terephthalate, comprising utilizing dimethyl terephthalate recovered by the separation and recovery process of any one of claims 1 to 12, as a starting material for production of bis(β-hydroxyethyl) terephthalate.

15. A method for reutilization of recovered dimethyl terephthalate, comprising utilizing dimethyl terephthalate recovered by the separation and recovery process of any one of claims 1 to 12, as a starting material for production of polyester.

* * * * *